United States Patent [19]

Spindler

[11] Patent Number: 5,583,241
[45] Date of Patent: Dec. 10, 1996

[54] FLUOROALKYL-SUBSTITUTED FERROCENYL DIPHOSPHINES AS LIGANDS FOR HOMOGENEOUS CATALYSTS

[75] Inventor: Felix Spindler, Starrkirch-Wil, Switzerland

[73] Assignee: Ciba-Geigy Corporation, Tarrytown, N.Y.

[21] Appl. No.: 313,485

[22] Filed: Sep. 27, 1994

[30] Foreign Application Priority Data

Oct. 1, 1993 [CH] Switzerland ............. 2972/93

[51] Int. Cl.$^6$ ....................................... C07F 17/02
[52] U.S. Cl. ........................ 556/11; 556/13; 556/14; 556/22; 556/143; 502/152; 502/158; 526/943
[58] Field of Search ................... 556/11, 13, 14, 556/22, 143; 526/943; 502/152, 158

[56] References Cited

U.S. PATENT DOCUMENTS

| | | | |
|---|---|---|---|
| 5,245,064 | 9/1993 | Gassman et al. | 556/60 |
| 5,371,256 | 12/1994 | Togni et al. | 556/14 |
| 5,466,844 | 11/1995 | Spindler et al. | 556/11 |

FOREIGN PATENT DOCUMENTS 0612758   8/1994   European Pat. Off. .

OTHER PUBLICATIONS

T. Hayashi et al. Bull. Chem. Soc. Jpn., 53, pp. 1138–1151 (1980).

*Primary Examiner*—Porfirio Nazario-Gonzalez
*Attorney, Agent, or Firm*—Kevin T. Mansfield

[57] ABSTRACT

Compounds of formula I

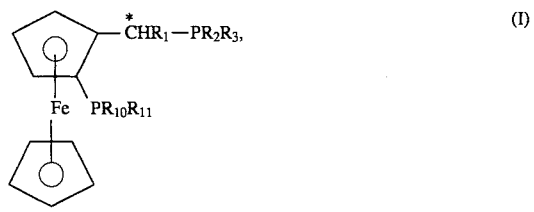

wherein $R_1$ is $C_1$–$C_8$alkyl, phenyl or phenyl which is substituted by 1 to 3 $C_1$–$C_4$alkyl or $C_1$–$C_4$alkoxy groups; $R_2$ is a radical of formula II

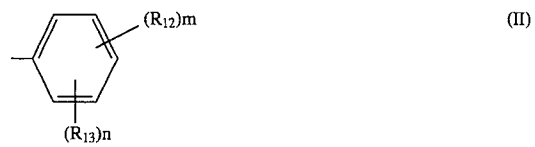

wherein $R_{12}$ is $C_1$–$C_5$alkyl which is partially or completely fluorinated;

$R_{13}$ is $C_1$–$C_4$alkyl, $C_1$–$C_4$alkoxy, —$SiR_4R_5R_6$, halogen, —$SO_3M$, —$CO_2M$, —$PO_3M$, —$NR_7R_8$ or —$[^\oplus NR_7R_8R_9]X^\ominus$;

m is an integer from 1 to 3, n is 0 or an integer from 1 to 4, and the sum of m+n is 1 to 5;

$R_3$, $R_{10}$, $R_{11}$ have each independently of one another the same meaning as $R_2$ or are each independently of one another $C_1$–$C_{12}$alkyl, $C_5$–$C_{12}$cycloalkyl, phenyl, $C_1$–$C_4$alkyl- or $C_1$–$C_4$alkoxy-substituted $C_5$–$C_{12}$cycloalkyl, or phenyl which is substituted by one to three identical or different members selected from the group consisting of $C_1$–$C_4$alkyl, $C_1$–$C_4$alkoxy, —$SiR_4R_5R_6$, halogen, —$SO_3M$, —$CO_2M$, —$PO_3M$, —$NR_7R_8$ and —$[^\oplus NR_7R_8R_9]X^\ominus$;

$R_4$, $R_5$ and $R_6$ are each independently of one another $C_1$–$C_{12}$alkyl or phenyl;

$R_7$ and $R_8$ are H, $C_1$–$C_{12}$alkyl or phenyl or $R_7$ and $R_8$, taken together, are tetramethylene, pentamethylene or 3-oxa-1,5-pentylene;

$R_9$ is H or $C_1$–$C_4$alkyl,

M is H or an alkali metal, $X^\ominus$ is the anion of a monobasic acid, and * is a stereogenic carbon atom, in the form of their racemates and diastereoisomers or mixtures of diastereoisomers. Rhodium and iridium complexes with these ligands are suitable for use as homogeneous enantioselective catalysts for the hydrogenation of prochiral compounds containing carbon double bonds or carbon/hetero atom double bonds.

21 Claims, No Drawings

FLUOROALKYL-SUBSTITUTED FERROCENYL DIPHOSPHINES AS LIGANDS FOR HOMOGENEOUS CATALYSTS

The present invention relates to 1-[2-(phosphino)ferrocenyl]alkylidene phosphines in the form of racemates and stereoisomers, to a process for their preparation, to iridium and rhodium complexes containing these ligands, and to the use thereof as enantioselective hydrogenation catalysts for the homogeneous hydrogenation of prochiral unsaturated compounds.

T. Hayashi et al. describe in Bull. Chem. Soc. Jpn., 53, pages 1136–1151, the preparation of a chiral ferrocenyl phosphine as ligand for transition metal complexes for asymmetric synthesis, namely [(R)-[(S)-2-(diphenylphosphino)ferrocenyl]ethyl]diphenylphosphine. Utilities for these compounds have not been described.

It has now been found that fluoroalkyl-substituted 1-[2-(phosphino)ferrocenyl]alkylidene phosphines are effective catalysts for asymmetrical hydrogenation and that a high enantioselectivity can be achieved with short reaction times. A further advantage of these compounds is that the rhodium and, in particular, iridium, complexes prepared therefrom have only a minor tendency to deactivation, so that hydrogenation reactions can be carried out at elevated temperatures, thereby resulting in a greater catalyst productivity.

In one of its aspects, the invention relates to compounds of formula I

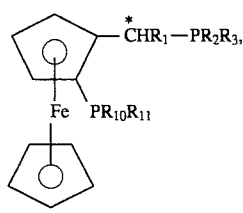
(I)

wherein $R_1$ is $C_1$–$C_8$alkyl, phenyl or phenyl which is substituted by 1 to 3 $C_1$–$C_4$alkyl or $C_1$–$C_4$alkoxy groups;

$R_2$ is a radical of formula II

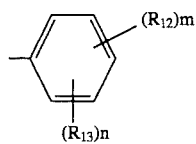
(II)

wherein $R_{12}$ is $C_1$–$C_5$alkyl which is partially or completely fluorinated;

$R_{13}$ is $C_1$–$C_4$alkyl, —$SiR_4R_5R_6$, halogen, —$SO_3M$, —$CO_2M$, —$PO_3M$, —$NR_7R_8$ or —$[^\oplus NR_7R_8R_9]X^\ominus$;

m is an integer from 1 to 3, n is 0 or an integer from 1 to 4, and the sum of m+n is 1 to 5;

$R_3$, $R_{10}$, $R_{11}$ have each independently of one another the same meaning as $R_2$ or are each independently of one another $C_1$–$C_{12}$alkyl, $C_5$–$C_{12}$cycloalkyl, phenyl, $C_1$–$C_4$alkyl- or $C_1$–$C_4$alkoxy-substituted $C_5$–$C_{12}$cycloalkyl, or phenyl which is substituted by one to three identical or different members selected from the group consisting of $C_1$–$C_4$alkyl, $C_1$–$C_4$alkoxy, —$SiR_4R_5R_6$, halogen, —$SO_3M$, —$CO_2M$, —$PO_3M$, —$NR_7R_8$ and —$[^\oplus NR_7R_8R_9]X^\ominus$;

$R_4$, $R_5$ and $R_6$ are each independently of one another $C_1$–$C_{12}$alkyl or phenyl;

$R_7$ and $R_8$ are H, $C_1$–$C_{12}$alkyl or phenyl or $R_7$ and $R_8$, taken together, are tetramethylene, pentamethylene or 3-oxa-1,5-pentylene;

$R_9$ is H or $C_1$–$C_4$alkyl,

M is H or an alkali metal, $X^\ominus$ is the anion of a monobasic acid, and * is a stereogenic carbon atom, in the form of their racemates and diastereoisomers or mixtures of diastereoisomers.

In formula II, m is preferably 1 or 2 and n is 0, 1 or 2. Preferably n is 0.

$R_1$ defined as alkyl may be linear or branched and contains preferably 1 to 4 carbon atoms. Typical examples are methyl, ethyl, n- and isopropyl, n-, iso- and tert-butyl, pentyl, hexyl, heptyl and octyl. Methyl and ethyl are preferred and methyl is especially preferred.

$R_1$ defined as substituted phenyl preferably contains 1 or 2 substituents. Alkyl substituents may typically be methyl, ethyl, n- and isopropyl, n-, iso- and tert-butyl. Methyl and ethyl are preferred. Alkoxy substituents may be methoxy, ethoxy, n- and isopropoxy, n-, iso- and tert-butoxy. Methoxy and ethoxy are preferred. In a preferred group of compounds of formula I, $R_1$ is preferably phenyl or phenyl which is substituted by one or two $C_1$–$C_4$alkyl or $C_1$–$C_4$alkoxy groups.

$R_3$, $R_{10}$ and $R_{11}$ defined as alkyl may be linear or branched and contain preferably 1 to 8, most preferably 1 to 4, carbon atoms. Typical examples are methyl, ethyl, n- and isopropyl, n-, iso- and tert-butyl, pentyl, hexyl, heptyl, octyl nonyl, decyl, undecyl and dodecyl. Methyl, ethyl, n- and isopropyl, n-, iso- and tert-butyl are preferred. When $R_2$ and $R_3$ and/or $R_{10}$ and $R_{11}$ are identical and have the significance of alkyl, they are most preferably isopropyl or tert-butyl.

$R_3$, $R_{10}$ and $R_{11}$ defined as cycloalkyl preferably contain 5 to 8, most preferably 5 or 6, ring carbon atoms. Exemplary of cycloalkyl are cyclopentyl, cyclohexyl, cycloheptyl, cyclooctyl, cyclodecyl and cyclododecyl. Cyclopentyl and cyclohexyl are preferred and cyclohexyl is especially preferred.

Cycloalkyl may be substituted, conveniently by 1 to 3 alkyl or alkoxy groups. Examples of such substituents have been indicated above. Methyl and ethyl are preferred, as are also methoxy and ethoxy. Substituted cycloalkyl is typically methyl- and methoxycyclopentyl and methyl- and methoxycyclohexyl.

$R_3$, $R_{10}$ and $R_{11}$ defined as substituted phenyl will preferably contain 1 or 2 substituents. If phenyl contains 2 or 3 substituents, these may be identical or different.

Examples of alkyl and alkoxy substituents have been indicated above. Preferred alkyl and alkoxy substituents of phenyl are methyl and ethyl as well as methoxy and ethoxy.

Halogen as a substituent of phenyl may preferably be selected from the group consisting of —F, —Cl and —Br.

$R_4$, $R_5$ and $R_6$ may be linear or branched alkyl that preferably contains 1 to 8 and, most preferably, 1 to 4, carbon atoms. Exemplary alkyl substituents have been indicated above. Preferably alkyl is methyl, ethyl, n-propyl, n-butyl and tert-butyl. The substituent —$SiR_4R_5R_6$ is most preferably trimethylsilyl.

Among the acid phenyl substituents —$SO_3M$, —$CO_2M$ and —$PO_3M$, the —$SO_3M$ group is preferred. M is preferably H, Li, Na and K.

$R_7$ and $R_8$ defined as alkyl preferably contain 1 to 6, most preferably 1 to 4, carbon atoms. Alkyl is preferably linear. Preferred examples are methyl, ethyl, n-propyl and n-butyl. $R_9$ defined as alkyl is preferably methyl.

$X^\ominus$ as anion of a monobasic acid is preferably $Cl^\ominus$, $Br^\ominus$ or the anion of a carboxylic acid, typically formate, acetate, trichloroacetate or trifluoroacetate.

Illustrative examples of substituted phenyl are 2-methylphen-1-yl, 3-methylphen-1-yl, 4-methylphen-1-yl, 2- or 4-ethylphen-1-yl, 2- or 4-isopropylphen-1-yl, 2- or 4-tert-butylphen-1-yl, 2-methoxyphen-1-yl, 3-methoxyphen-1-yl, 4-methoxyphen-1-yl, 2- or 4-ethoxyphen-1-yl, 4-trimethylsilylphen-1-yl, 2- or 4-fluorophen-1-yl, 2,4-difluorophen-1-yl, 2- or 4-chlorophen-1-yl, 2,4-dichlorophen-1-yl, 2,4-dimethylphen-1-yl, 3,5-dimethylphen-1-yl, 2-methoxy-4-methylphen-1-yl, 3,5-dimethyl-4-methoxyphen-1-yl, 3,5-dimethyl-4-(dimethylamino)phen-1-yl, 2- or 4-aminophen-1-yl, 2- or 4-methylaminophen-1-yl, 2- or 4-(dimethylamino)phen-1-yl, 2- or 4-$SO_3H$-phen-1-yl, 2- or 4-$SO_3Na$-phen-1-yl, 2- or 4-[$^{\ominus}NH_3Cl^{\oplus}$]phen-1-yl, 3,4,5-trimethylphen-1-yl or 2,4,6-trimethylphen-1-yl.

$R_{12}$ is preferably $C_1$–$C_3$alkyl, most preferably $C_1$–$C_2$alkyl, which is partially or completely fluorinated. Illustrative examples of partially fluorinated $C_1$–$C_5$alkyl are the position isomers of mono- to decafluoropentyl, mono- to octafluorobutyl, mono- to hexafluoropropyl, mono- to tetrafluoroethyl as well as mono- and difluoromethyl. Among the partially fluorinated alkyl radicals, those of formulae —$CF_2H$ and —$CF_2(C_1$–$C_4$alkyl) are particularly preferred. $R_{12}$ is most preferably a perfluorinated alkyl radical. Typical examples of such radicals are perfluoropentyl, pefluorobutyl, perfluoropropyl, perfluoroethyl and, preferably, trifluoromethyl. The fluorinated alkyl groups are preferably located in the 3-, 4- and 5-positions.

In a particularly preferred embodiment, $R_2$ is 4-trifluoromethylphenyl or 3,5-bis(trifluoromethyl)phenyl.

When n is 1, $R_{13}$ is preferably $C_1$–$C_4$alkyl or $C_1$–$C_4$alkoxy. Preferably n is 0. Representative examples of preferred alkyl and alkoxy radicals have been cited above.

In a preferred embodiment, $R_3$, $R_{10}$ and $R_{11}$ are identical and are phenyl, cyclohexyl, tert-butyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl and 3,5-dimethyl-4-methoxyphen-1-yl.

$R_2$ and $R_3$ are most preferably identical substituents and are a radical of formula II, wherein $R_{10}$ und $R_{11}$ are preferably identical substituents and are phenyl, cyclohexyl, tert-butyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl or 3,5-dimethyl-4-methoxyphen-1-yl.

In a further preferred embodiment, $R_2$ and $R_3$ are identical substituents and are a radical of formula II, $R_{10}$ is phenyl and $R_{11}$ is cyclohexyl, 2- or 4-methylphen-1-yl, 2- or 4-methoxyphen-1-yl, 4-(dimethylamino)phen-1-yl, 3,5-dimethyl-4-(dimethylamino)phen-1-yl, 3,5-dimethyl-4-methoxyphen-1-yl or 4-tert-butylphen-1-yl.

When $R_2$ and $R_3$ are identical and are the radical of formula II, $R_1$ is most preferably methyl and $R_{10}$ and $R_{11}$ are phenyl or cyclohexyl.

In another preferred embodiment, $R_2$, $R_3$, $R_{10}$ and $R_{11}$ are identical and are a radical of formula II.

Compounds of formula I are very particularly preferred wherein $R_1$ is methyl, $R_2$, $R_3$, $R_{10}$ and $R_{11}$ are identical and are a radical of formula II;

$R_{12}$ is 4-trifluoromethyl or 3,5-bis(trifluoromethyl) and n is 0. In another particularly preferred embodiment, $R_1$ is methyl, $R_2$ and $R_3$ are identical and are a radical of formula II, $R_{10}$ and $R_{11}$ are phenyl, $R_{12}$ is 4-trifluoromethyl or 3,5-bis(trifluoromethyl) and n is 0.

Particularly preferred compounds of formula I are typically:

{(R)-1-[(S)-2-diphenylphosphino)ferrocenyl]}ethyl bis(4-trifluoromethylphenyl)phosphine {(R)-1-[(S)-2-diphenylphosphino)ferrocenyl]}ethyl bis(3,5-bis(trifluoromethyl)phenyl)phosphine, {(R)-1-[(S)-2-bis(4-trifluoromethylphenyl)phosphino)ferrocenyl]}ethyl bis(4-trifluoromethylphenyl)phosphine, {(R)-1-[(S)-2-bis(4-trifluoromethylphenyl)phosphino)ferrocenyl]}ethyl bis(3,5-dimethylphenyl)phosphine, {(R)-1-[(S)-2-bis(4-trifluoromethylphenyl)phosphino)ferrocenyl]}ethyl dicyclohexylphosphine, {(R)-1-[(S)-2-bis(3,5-bis(trifluoromethyl)phenyl)phosphino)ferrocenyl]}ethyl bis(3,5-dimethylphenyl)phosphine, {(R)-1-[(S)-2-bis(3,5-bis(trifluoromethyl)phenyl)phosphino)ferrocenyl]}ethyl diphenylphosphine, {(R)-1-[(S)-2-bis(4-trifluoromethylphenyl)phosphino)ferrocenyl]}ethyl diphenylphosphine.

The compounds of formula I are prepared either by reacting a compound of formula III

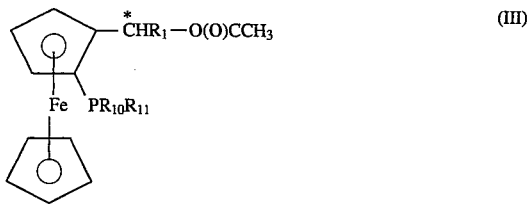

in the presence of an inert solvent, at room temperature or elevated temperature, with a phosphine of formula IV

or reacting a compound of formula VII

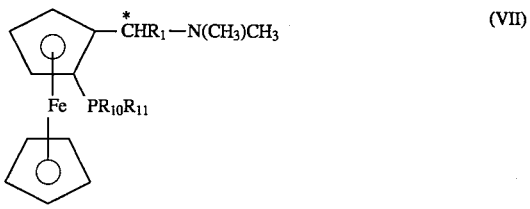

wherein $R_1$, $R_{10}$ and $R_{11}$ are as defined for formula I, in the presence of an inert solvent, at room temperature or elevated temperature, with a phosphine of formula IV

This process constitutes a further object of the invention.

The reactions are known per se and are described by T. Hayashi et al. im Bull. Chem. Soc. Jpn., 53, pp. 1136–1151. The preparation of all stereoisomers of compounds of formulae III and VII is also described in this reference or can be carried out in analogous manner. The phosphines of formula IV are known or are obtainable by known methods in analogous manner.

The reaction temperature may be in the range from 20° to 150° C., preferably from 40 to 100° C. Suitable solvents are polar protic and aprotic solvents, which may be used singly or as mixtures of two or more solvents. Typical examples of solvents are alkanols such as methanol and ethanol, and carboxylic acids such as formic acid and acetic acid.

The compounds of formula I are obtained as racemates, mixtures of stereoisomers or as stereoisomers, depending on whether the compounds of formula III are used as racemates, mixtures of stereoisomers or as stereoisomers. Racemates and mixtures of stereoisomers can be separated by known methods into the stereoisomers, preferably as a rule by chromatographic methods.

The compounds of formula I are isolated and purified by per se known methods, typicallyby distillation, extraction, crystallisation and/or chromatographic methods.

The compounds of formula I are suitable for use as ligands for rhodium and iridium complexes. In another of its aspects, the invention relates to complexes of formulae V and VI

wherein $X_1$ is two $C_2$–$C_{12}$olefins or a $C_5$–$C_{12}$diene, Z is Cl, Br or I, $A_1^{\ominus}$ is the anion of an oxyacid or of a complex acid, $M_1$ is Rh or Ir, and Y is a diphosphine of formula I. The complexes of formula VI are preferred.

With respect to the diphosphines of formula I, the same preferences and exemplifications apply as stated previously. $X_1$ as olefin preferably contains 2 to 6 and, most preferably, 2 to 4, carbon atoms. Ethylene is particularly preferred. Further examples are propene and 1-butene. $X_1$ as diene preferably contains 5 to 8 carbon atoms. The diene may be an open-chain or mono- or bicyclic diene. The two olefinic groups of the diene are preferably linked through one or two $CH_2$ groups. Typical examples are 1,3-pentadiene, cyclopentadiene, 1,5-hexadiene, 1,4-cyclohexadiene, 1,4-or 1,5-heptadiene, 1,4- or 1,5-cycloheptadiene, 1,4- or 1,5-octadiene, 1,4- or 1,5-cyclooctadiene, norbornadiene. $X_1$ is preferably two ethylene, 1,5-hexadiene, 1,5-cyclooctadiene or norbornadiene.

Z in formula V is preferably Cl or Br. Typical examples of $A_1^{\ominus}$ in formula VI are $ClO_4^{\ominus}$, $FSO_3^{\ominus}$, $CH_3SO_3^{\ominus}$, $BF_4^{\ominus}$, $PF_6^{\ominus}$, $SbCl_6^{\ominus}$, $AsF_6^{\ominus}$ and $SbF_6^{\ominus}$. Preferably $A_1$ is $^{\ominus}ClO_4^{\ominus}$, $CF_3SO_3^{\ominus}$, $BF_4^{\ominus}$, $PF_4^{\ominus}$ and $SbF_6^{\ominus}$.

The novel complexes are obtained in per se known manner by the reaction of equimolar amounts of a compound of formula I with a metal complex of formula $[M_1(X_1)Z]_2$ or $M_1(X_1)_2^{\oplus}A_1^{\ominus}$, wherein $M_1$, $X_1$, Z and $A_1^{\ominus}$ have the meanings previously assigned to them. The metal complexes are known, in which connection reference is made, inter alia, to EP-A-0 302 021 and US-A-5 011 995.

The reaction is conveniently carried out under an inert gas atmosphere, typically argon, and expediently in the temperature range from 0° to 40° C., preferably at room temperature. The concurrent use of a solvent or mixture of solvents is advantageous, conveniently selected from the group consisting of hydrocarbons (benzene, toluene, xylene), halogenated hydrocarbons (methylene chloride, chloroform, chlorobenzene), alkanols (methanol, ethanol, 2-methoxyethanol), and ethers (diethyl ether, dibutyl ether, 1, 2-dimethoxyethane, tetrahydrofuran, dioxane) or mixtures thereof. The novel complexes can be isolated and purified by conventional methods, or they can be prepared in situ prior to hydrogenation and then used in dissolved form direct as hydrogenation catalysts.

The novel complexes are preeminently suitable for use as homogeneous catalysts for the enantioselective hydrogenation of prochiral compounds containing carbon double bonds and carbon/hetero atom double bonds, typically compounds that contain a group selected from C=C, C=N, C=O, C=C—N and C=C—O [q.v. inter alia K. E. König, The Applicability of Asymmetric Homogeneous Catalysis, in James D. Morrison (ed.), Asymmetric Synthesis, Vol. 5, Academic Press, 1985]. Examples of such compounds are prochiral olefins, enamines, imines and ketones. Surprisingly high yields are obtained, normally even a quantitative chemical conversion, in short reaction times. Particularly surprising are the very high optical yields which are obtained with the novel complexes. The enantiomer excess (ee) may be more than 90%. It is possible to use racemates, mixtures of stereoisomers or stereoisomers of the complexes of formulae V and VI, mixtures of stereoisomers or stereoisomers being preferred.

In another of its aspects, the invention relates to the use of the novel complexes of formulae V and VI as homogeneous catalysts for the asymmetric hydrogenation of prochiral compounds containing carbon double bonds or carbon/hereto atom double bonds, especially those containing a C=C, C=N, C=O, C=C—N or C=C—O group. The preferred utility is for hydrogenating unsymmetric carbon double bonds, ketimines and ketones. The catalyst of formulae V and VI in the form of the iridium complex is also preferred for hydrogenating prochiral N-arylketimines to optically active secondary amines. The catalyst of formulae V and VI in the form of the rhodium complex is preferably used for hydrogenating carbon double bonds, for example prochiral carbon double bonds.

In yet another of its aspects, the invention provides a process for the asymmetric hydrogenation of prochiral compounds containing carbon double bonds or carbon/hetero atom double bonds under homogeneous reaction conditions, which process comprises hydrogenating said compounds in the temperature range from −20° to +80° C., and under a hydrogen pressure of $10^4$ to $10^7$ Pa, in the presence of a catalytic amount of a complex of formula V or VI.

Preferred prochiral compounds are those previously mentioned. Unsymmetric ketimines and ketones are known. Suitable N-arylketimines are disclosed, inter alia, in EP-A-0 256 982. N-Aliphatic ketimines are disclosed, inter alia, in EP-A-0 301 457. Such imines can be prepared from the corresponding unsymmetric ketones, which are known and commercially available or obtainable by known methods. Suitable substituted alkenes are described in the publication of K. E. König referred to above.

The process is preferably carried out in the temperature range from −10° to 50° C. and preferably under a hydrogen pressure of $1.10^5$ to $6.10^6$ Pa.

The amount of catalyst is preferably chosen such that the molar ratio of compound to be hydrogenated (substrate) to the complex of formula V or VI is preferably 100 000 to 20, more particularly 200 00 to 40 and, most preferably, 1000 to 50.

A preferred mode of carrying out the process comprises the additional concurrent use of an ammonium or alkali metal chloride, bromide or iodide, especially when using the novel iridium catalysts. The amount may typically be 0.1 to 100, preferably 1 to 50 and, most preferably, 2 to 20, equivalents, based on the complex of formula V or VI. The addition of iodides is preferred. Ammonium is preferably tetraalkylammonium containing 1 to 6 carbon atoms in the alkyl groups, and the preferred alkali metal is lithium, sodium and potassium.

The hydrogenation can be carried out without, or in the presence of, a solvent. Suitable solvents, which may be used alone or in admixture, are typically: aliphatic and aromatic hydrocarbons (pentane, hexane, cyclohexane, methylcyclohexane, benzene, toluene, xylene), alcohols such as methanol, ethanol, propanol and butanol; ethers such as diethyl ether, 2-methoxyethyl ether, 1,2-dimethoxyethane, tetrahydrofuran and dioxane; halogenated hydrocarbons such as methylene chloride, chloroform, 1,1,2,2-tetrachloroethane and chlorobenzene; esters and lactones such as ethyl acetate, butyrolactone or valerolactone; carboxamides and lactams such as dimethyl formamide, dimethyl acetamide and N-methylpyrrolidone. Preferred mixtures are those of alcohols and aromatic hydrocarbons, typically methanol/benzene or methanol/toluene. The preferred solvent is methanol by itself or in admixture with benzene or toluene.

The novel hydrogenation process makes it possible to obtain optically pure compounds which are useful intermediates for the synthesis of biologically active compounds, especially in the pharmaceutical and agrochemical sectors. Thus, for example, herbicidally active 5-imidazolecarboxylic acid derivatives which can be used for weed control (EP-A-0 207 563) can be prepared from secondary amines, especially N-carbalkoxymethylamines. The optically pure α-aminocarboxylates are suitable for peptide syntheses. Optically pure aminocarboxylic acids which are useful synthesis components can be obtained from unsaturated aminocarboxylic acids.

The following Examples illustrate the invention in more detail. The chemical conversion is determined by gas chromatography [column DB 17/30 W (15 m), supplier: JCW Scientific INC., USA, temperature program: 60° C./1 min up to 220° C., ΔT: 10°·min$^{-1}$]. The determination of the optical yield, enantiomer excess ee), is made by gas chromatography [columns Chirasil-Val, 50 m, FS-Lipodex (50 m)] or by HPLC (stationary phase: Chiralcel OD).

Preparation of the compounds of formula I

EXAMPLE A1

{(R)-1-[(S)-2-diphenylphosphino)ferrocenyl]}ethyl bis(4-trifluoromethylphenyl)phosphine (A).

1.2 g (2.73 mmol) of N-{(R)-1-[(S)-diphenylphosphino)ferrocenyl]}ethyl dimethylamine [prepared according to Bull. Chem. Soc. Jpn., 53, 1138 (1980)], 25 ml of acetic acid and 1 g (3.1 mmol) of bis(4-trifluoromethylphenyl)phosphine are charged in succession to a 50 ml Schlenk flask under argon, and the mixture is then heated for 60 minutes, with stirring, at 100° C. The crude product is then extracted with water/toluene. The organic phase is dried over magnesium sulfate and the solvent is removed on a rotary evaporator. The residue is chromatographed on silica gel (solvent: hexane/dichlormethane (4:1)). Recrystallisation of the crude product from hot ethanol gives 1.49 g of A (yield 76%) as an orange-yellow crystalline substance.

$^{-}$P-NMR (CDCl$_3$): −26.4 (d, J=24), 6.6 (d, J=24).

EXAMPLE A2

{(R)-1-[(S)-2-diphenylphosphino)ferrocenyl]}ethyl bis(3,5-bis(trifluoromethyl)phenyl)phosphine (B).

The general procedure of Example A1 is repeated, but modifying the reaction conditions as follows:

Reaction of 0.85 g (1.92 mmol) of N-{(R)-1-[(S)-diphenylphosphino)ferrocenyl]}ethyl dimethylamine, 1.0 g (2.18 mmol) of bis(3,5-bis(trifluoromethyl)phenyl)phosphine and 17 ml of acetic acid, to give 1.30 g of B (yield: 80%) as an orange crystalline substance.

$^{-}$P-NMR (CDCl$_3$): −27.4 (d, J=30), 8.8 (d, J=30).

BEISPIEL A3

{(R)-1-[(S)-2-bis(4-trifluoromethylphenyl) phosphino)ferrocenyl]}ethyl bis-(4-trifluoromethylphenyl)phosphine (C).

The general procedure of Example A1 is repeated, but modifying the reaction conditions as follows:

Reaction of 4.28 g (7.42 mmol) of N-{(R)-1-[(S)-bis(4-trifluoromethylphenyl)phosphino)ferrocenyl]}ethyl dimethylamine [prepared from N-[(R)-1-ferrocenyl]ethyl dimethylamine and bis(4-trifluoromethylphenyl)phosphine chloride in accordance with Bull. Chem. Soc. Jpn., 53, 1138 (1980)], 2.75 g (8.53 mmol) of bis(4-trifluoromethylphenyl)phosphine and 55 ml of acetic acid, to give 5.89 g of C (yield: 93%).

$^{-}$P-NMR (CDCl$_3$): −25.7 (d, J=30), 8.4 (d, J=30)

EXAMPLE A4

{(R)-1-[(S)-2-bis(4-trifluoromethylphenyl) phosphino)ferrocenyl]}ethyl bis-(3,5-dimethylphenyl)phosphine (D).

The general procedure of Example A1 is repeated, but modifying the reaction conditions as follows:

Reaction of 1.21 g (2.1 mmol) of N-{(R)-1-[(S)-bis(4-trifluoromethylphenyl)phosphino)ferrocenyl]}ethyl dimethylamine [prepared from N-[(R)-1-ferrocenyl]ethyl dimethylamine and bis(4-trifluoromethylphenyl)phosphine chloride in accordance with Bull. Chem. Soc. Jpn., 53, 1138 (1980)], 0.53 g (2.2 mmol) of bis(3,5-dimethylphenyl)phosphine and 15 ml of acetic acid, to give 460 mg of (D) as an orange crystalline substance (yield: 28%).

$^{-}$P-NMR (CDCl$_3$): −24.7 (d, J=23), 8.7 (d, J=23).

EXAMPLE A5

{(R)-1-[(S)-2-bis(4-trifluoromethylphenyl) phosphino)ferrocenyl]}ethyl dicyclohexylphosphine (E).

The general procedure of Example A1 is repeated, but modifying the reaction conditions as follows:

Reaction of 1.73 g (3.0 mmol) of N-{(R)-1-[(S)-bis(4-trifluoromethylphenyl)phosphino)ferrocenyl]}ethyl dimethylamine [prepared from N-[(R)-1-ferrocenyl]ethyl dimethylamine and bis(4-trifluoromethylphenyl)phosphine chloride in accordance with Bull. Chem. Soc. Jpn., 53, 1138 (1980)], 0.69 g (3.4 mmol) of dicyclohexylphosphine and 20 ml of acetic acid, to give 1.69 g of (E) as an orange crystalline substance (yield: 77%).

$^{-}$P-NMR (CDCl$_3$): −25.5 (d, J=42), 15.65 (d, J=42).

EXAMPLE A6

{(R)-1-[(S)-2-bis(3,5-bis(trifluoromethyl)phenyl) phosphino)ferrocenyl]}ethyl bis(3,5-dimethylphenyl)phosphine (F)

The general procedure of Example A1 is repeated, but modifying the reaction conditions as follows:

Reaction of 1.07 g (1.5 mmol) of N-{(R)-1-[(S)-bis(3,5-bis(trifluoromethyl)phenyl)phosphino)ferrocenyl]}ethyl dimethylamine [prepared in accordance with Bull. Chem. Soc. Jpn., 53, 1138 (1980)], 0.41 g (1.7 mmol) of bis(3,5-dimethylphenyl)phosphine and 15 ml of acetic acid, to give 0.95 g of F (69.3% of theory) as an orange crystalline substance.

⁻P-NMR (CDCl₃): −22.8 (d, J=35), 11.7 (d, J=35).

EXAMPLE 7

{(R)-1-[(S)-2-bis(3,5-bis(trifluoromethyl)
phenyl)phosphino)ferrocenyl]}ethyl
diphenylphosphine (G)

The general procedure of Example A1 is repeated, but modifying the reaction conditions as follows:

Reaction of 1.0 g (1.4 mmol) of N-{(R)-1-[(S)-bis(3,5-bis(trifluoromethyl)phenyl)phosphino)ferrocenyl]}ethyl dimethylamine [prepared in accordance with Bull. Chem. Soc. Jpn., 53, 1138 (1980)], 0.3 g (1.6 mmol) of diphenylphosphine and 14 ml of acetic acid, to give 1.1 g of G (91.7% of theory) as an orange crystalline substance.

⁻P-NMR (CDCl₃): −22.9 (d, J=36), 10.7 (d, J=36).

EXAMPLE A8

{(R)-1-[(S)-2-bis(3,5-bis(trifluoromethyl)
phenyl)phosphino)ferrocenyl]}ethyl
bis(3-methoxyphenyl)phosphine (H)

The general procedure of Example A1 is repeated, but modifying the reaction conditions as follows:

Reaction of 1.0 g (1.4 mmol) of N-{(R)-1-[(S)-bis(3,5-bis(trifluoromethyl)phenyl)phosphino)ferrocenyl]}ethyl dimethylamine [prepared in accordance with Bull. Chem. Soc. Jpn., 53, 1138 (1980)], 0.39 g (1.6 mmol) bis(3-methoxyphenyl)phosphine and 15 ml of acetic acid, to give 0.37 g of H (30.5% of theory) as an orange resin which is subsequently foamed from ether.

⁻P-NMR (CDCl₃): −23.0 (d, J=33), 12.2 (d, J=33).

EXAMPLE A9

{(R)-1-[(S)-2-bis(3,5-dimethylphenyl)
phosphino)ferrocenyl]}ethyl
bis(3,5-bis(trifluoromethyl)phenyl) phosphine (I)

The general procedure of Example A1 is repeated, but modifying the reaction conditions as follows:

Reaction of 1.0 g (2.0 mmol) of Reaction of N-{(R)-1-[(S)-bis(3,5-dimethylphenyl)phosphino)ferrocenyl]}ethyl dimethylamine [prepared in accordance with Bull. Chem. Soc. Jpn., 53, 1138 (1980)], 1.05 g (2.3 mmol) of bis(3,5-bis(trifluoromethyl)phenyl)phosphine and 15 ml of acetic acid, to give 310 mg of I (17% of theory) as an orange crystalline substance.

⁻P-NMR (CDCl₃): −27.1 (d, J=30), 9.3 (d, J=30).

EXAMPLE A10

{(R)-1-[(S)-2-bis(4-trifluoromethylphenyl)
phosphino)ferrocenyl]}ethyl diphenylphosphine (J)

The general procedure of Example A1 is repeated, but modifying the reaction conditions as follows:

Reaction of 1.04 g (1.8 mmol) of N-{(R)-1-[(S)-bis(4-trifluoromethylphenyl)phosphino)ferrocenyl]}ethyl dimethylamine [prepared in accordance with Bull. Chem. Soc. Jpn., 53, 1138 (1980)], 0.37 g (1.8 mmol) of diphenylphosphine and 15 ml of acetic acid, to give 1.03 g of J (80% of theory) as an orange crystalline substance.

⁻P-NMR (CDCl₃): −25.0 (d, J=27), 8.4 (d, J=27).

EXAMPLE A11

{(R)-1-[(S)-2-bis(4-trifluoromethylphenyl)
phosphino)ferrocenyl]}ethyl
bis(4-tert-butylphenyl)phosphine (K)

The general procedure of Example A1 is repeated, but modifying the reaction conditions as follows:

Reaction of 1.15 g (1.9 mmol) of N-{(R)-1-[(S)-bis(4-trifluoromethylphenyl)phosphino)ferrocenyl]}ethyl dimethylamine [prepared in accordance with Bull. Chem. Soc. Jpn., 53, 1138 (1980)], 0.7 g (2.1 mmol) of bis(4-tert-butylphenyl)phosphine and 15 ml of acetic acid, to give 170 mg of K (10% of theory) as an orange crystalline substance.

⁻P-NMR (CDCl₃): −24.5 (d, J=30), 6.6 (d, J=30).

Use Examples

EXAMPLES B1

Preparation of N-(2'-methyl-6'-ethyl-phen-1'-yl)-
N-(1-methoxymethyl)ethylamine 24.1 mg (0.033 mmol) of A are added to a solution of 10.2 mg (0.015 mmol) of [Ir(1,5-cyclooctadien)Cl]₂ in 10 ml of a 3:1 solvent mixture of tetrahydrofuran and methylene chloride, and the mixture is stirred for 15 minutes. Separately, 5 ml (2.4 mmol) of N-(2'-methyl-6'oethylphen-1'-yl)-N-(1-methoxymethyl)eth-1-ylidene-amine are dissolved in 10 ml of tetrahydrofuran/methylene chloride (3:1). The imine and the catalyst solution are transferred in succession by a steel capillary to a 50 ml steel autoclave under inert gas. In three cycles (20 bar, normal pressure), the inert gas is expelled with hydrogen. Hydrogenation is then carried out under 25 bar and the autoclave is heated to 30° C. The reaction is discontinued after 6 hours. The chemical conversion is 100% and the optical yield is 56% (S).

EXAMPLE B2

Preparation of N-(2'-methyl-6'-ethylphen-1'-yl)-
N-(1-methoxymethyl)ethylamine

A mixture of 10.2 mg (0.015 mmol) of [Ir(1,5-cyclooctadiene)Cl]₂ and 28.5 mg (0.033 mmol) of B is covered with a layer of 5 ml (24 mmol) of N-(2'-methyl-6'-ethylphen-1'-yl)-N-(1-methoxymethyl)eth-1-ylidene-amine and then transferred by a steel capillary to a 50 ml steel autoclave. The general further procedure of Example B1 is carried out.

The reaction is discontinued after 6 hours. The chemical conversion is 87% and the enantiomer purity is 62% (S).

Examples B3–B17 of Tables 1 and 2 are carried out in general accordance with the procedure described in Example B1.

The following abbreviations are used in Tables 1 and 2:
Rh⁺=[Rh(norbornadiene)₂]BF4, Rh⁰=[Rh(norbornadiene)Cl]₂, Ir⁰=[Ir(1,5-cyclooctadiene)Cl]₂, S1: methyl-Z-2-acetamidocinnamate, S2: Z-2-acetamidocinnamic acid, S3: dimethyl itaconate, S4: methyl acetylacetate, S5: ethyl pyruvate; S6: N-(2'-methyl-6'-ethylphen-1'-yl)-N-(1-methoxymethyl)eth-1-ylidene-amine, M/T: MeOH/toluene (1:1), *) addition of 150 mg of tetrabutylammonium iodide.

TABLE 1

| Ex. | Substr. (mmol) | Cat. | Ligand | S/C | Solv. | bar H$_2$ |
|---|---|---|---|---|---|---|
| B3  | S6 (24.4) | Ir$^0$ | C | 800 | — | 30 |
| B4  | S6 (24.4) | Ir$^0$ | D | 800 | i-PrOH | 25 |
| B5  | S1 (3.4)  | Rh$^+$ | E | 100 | MeOH | 1 |
| B6  | S2 (3.4)  | Rh$^+$ | E | 100 | MeOH | 1 |
| B7  | S3 (3.14) | Rh$^+$ | E | 200 | MeOH | 1 |
| B8  | S5 (4.4)  | Rh$^0$ | E | 200 | Toluol | 40 |
| B9  | S4 (4.3)  | Rh$^0$ | E | 200 | M/T | 20 |
| B10 | S1 (3.4)  | Rh$^+$ | G | 100 | MeOH | 50 |
| B11 | S2 (3.4)  | Rh$^+$ | G | 100 | MeOH | 50 |
| B12 | S1 (3.4)  | Rh$^+$ | H | 100 | MeOH | 50 |
| B13 | S4 (4.3)  | Rh$^0$ | B | 200 | M/T | 70 |
| B14 | S4 (4.3)  | Rh$^0$ | A | 200 | MeOH | 20 |
| B15 | S6 (24.4) | Ir$^0$* | F | 800 | iPrOH | 25 |
| B16 | S6 (24.4) | Ir$^0$* | B | 800 | — | 30 |
| B17 | S6 (24.4) | Ir$^0$* | G | 800 | i-PrOH | 25 |

TABLE 2

| Ex. | Substr. (mmol) | T[°C.] | Time h | Conv. % | e.e. (%) | (Config.) |
|---|---|---|---|---|---|---|
| B3  | S6 (24.4) | 25 | 24  | 82   | 67.4  | (S) |
| B4  | S6 (24.4) | 25 | 20  | 99   | 79.8  | (S) |
| B5  | S1 (3.4)  | 25 | 1   | 100  | 98    | (R) |
| B6  | S2 (3.4)  | 25 | 0,5 | 100  | 96.3  | (R) |
| B7  | S3 (3.14) | 25 | 0,5 | 100  | >99.5 | (S) |
| B8  | S5 (4.4)  | 10 | 41  | 91,5 | 56    | (S) |
| B9  | S4 (4.3)  | 25 | 44  | 98   | 77.3  | (S) |
| B10 | S1 (3.4)  | 40 | 65  | 96   | 83.5  | (R) |
| B11 | S2 (3.4)  | 25 | 10  | 100  | 73.6  | (R) |
| B12 | S1 (3.4)  | 40 | 21  | 100  | 73.6  | (R) |
| B13 | S4 (4.3)  | 25 | 93  | 98   | 52.3  | (S) |
| B14 | S4 (4.3)  | 25 | 85  | 50   | 78    | (S) |
| B15 | S6 (24.4) | 25 | 18  | 100  | 75.8  | (S) |
| R16 | S6 (24.4) | 25 | 24  | 97   | 61.6  | (S) |
| B17 | S6 (24.4) | 25 | 18  | 100  | 78.2  | (S) |

What is claimed is:

1. A compound of formula I

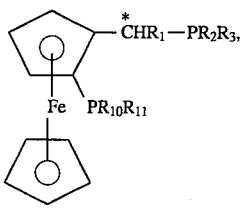

(I)

wherein

R$_1$ is C$_1$–C$_8$alkyl, phenyl or phenyl which is substituted by 1 to 3 C$_1$–C$_4$alkyl or C$_1$–C$_4$alkoxy groups;

R$_2$ is a radical of formula II

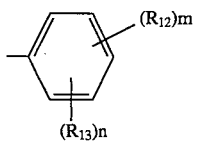

(II)

wherein

R$_{12}$ is C$_1$–C$_5$alkyl which is partially or completely fluorinated;

R$_{13}$ is C$_1$–C$_4$alkyl, C$_1$–C$_4$alkoxy, —SiR$_4$R$_5$R$_6$, halogen, —SO$_3$M, —CO$_2$M, —PO$_3$M, —NR$_7$R$_8$ or —[$^\oplus$NR$_7$R$_8$R$_9$]X$^\ominus$;

m is an integer from 1 to 3, n is 0 or an integer from 1 to 4, and the sum of m+n is 1 to 5;

R$_3$, R$_{10}$, R$_{11}$ have each independently of one another the same meaning as R$_2$ or are each independently of one another C$_1$–C$_{12}$alkyl, C$_5$–C$_{12}$cycloalkyl, phenyl, C$_1$–C$_4$alkyl- or C$_1$–C$_4$alkoxy-substituted C$_5$–C$_{12}$cycloalkyl, or phenyl which is substituted by one to three identical or different members selected from the group consisting of C$_1$–C$_4$alkyl, C$_1$–C$_4$alkoxy, —SiR$_4$R$_5$R$_6$, halogen, —SO$_3$M, —CO$_2$M, —PO$_3$M, NR$_7$R$_8$ and —[$^\oplus$NR$_7$R$_8$R$_9$]X$^\ominus$;

R$_4$, R$_5$ and R$_6$ are each independently of one another C$_1$–C$_{12}$alkyl or phenyl;

R$_7$ and R$_8$ are H, C$_1$–C$_{12}$alkyl or phenyl or

R$_7$ and R$_8$, taken together, are tetramethylene, pentamethylene or 3-oxa-1,5-pentylene;

R$_9$ is H or C$_1$–C$_4$alkyl,

M is H or an alkali metal, X$^\ominus$ is the anion of a monobasic acid, and * is a stereogenic carbon atom, in the form of the racemates or diastereoisomers thereof or of a mixture of diastercoisomers.

2. A compound of formula I according to claim 1, wherein R$_1$ as alkyl is linear.

3. A compound of formula I according to claim 2, wherein R$_1$ is C$_1$–C$_4$alkyl.

4. A compound of formula I according to claim 3, wherein R$_1$ is methyl or ethyl.

5. A compound of formula I according to claim 1, wherein R$_1$ is phenyl or phenyl which is substituted by one or two C$_1$–C$_4$alkyl or C$_1$–C$_4$alkoxy groups.

6. A compound of formula I according to claim 1, wherein R$_3$, R$_{10}$ and R$_{11}$ are C$_1$–C$_8$alkyl.

7. A compound of formula I according to claim 1, wherein R$_3$, R$_{10}$ and R$_{11}$ as cycloalkyl contain 5 to 8 ring carbon atoms.

8. A compound of formula I according to claim 7, wherein R$_3$, R$_{10}$ and R$_{11}$ as cycloalkyl are cyclopentyl or cyclohexyl.

9. A compound of formula I according to claim 1, wherein R$_3$, R$_{10}$ and R$_{11}$ are phenyl, 2-methylphen-1-yl, 3-methylphen-1-yl, 4-methylphen-1-yl, 2- or 4-ethylphen-1-yl, 2- or 4-isopropylphen-1-yl, 2- or 4-tert-butylphen-1-yl, 2-methoxyphen-1-yl, 3-methoxyphen-1-yl, 4-methoxyphen-1-yl, 2- or 4-ethoxyphen-1-yl, 4-trimethylsilylphen-1-yl, 2- or 4-fluorophen-1-yl, 2,4-difluorophen-1-yl, 2- or 4-chlorophen-1-yl, 2,4-dichlorophen-1-yl, 2,4-dimethylphen-1-yl, 3,5-dimethylphen-1-yl, 2-methoxy-4-methylphen-1-yl, 3,5-dimethyl-4-methoxyphen-1-yl, 3,5-dimethyl-4-(dimethylamino)phen-1-yl, 2- or 4-aminophen-1-yl, 2- or 4-methylaminophen-1-yl, 2- or 4-(dimethylamino)phen-1-yl, 2- or 4-SO$_3$H-phen-1-yl, 2- or 4-SO$_3$Na-phen-1-yl, 2- or 4-[$^\oplus$NH$_3$Cl$^\ominus$]phen-1-yl, 2,4,6-trimethylphen-1-yl or 3,4,5-trimethylphen-1-yl.

10. A compound of formula I according to claim 1, wherein R$_{12}$ is C$_1$–C$_3$perfluoroalkyl.

11. A compound of formula I according to claim 1, wherein R$_{13}$ is C$_1$–C$_4$alkyl or C$_1$–C$_4$alkoxy.

12. A compound of formula I according to claim 1, wherein R$_{12}$ is 4-trifluoromethyl or 3,5-bis(trifluoromethyl).

13. A compound of formula I according to claim 1, wherein R$_3$, R$_{10}$ and R$_{11}$ are identical and are phenyl, cyclohexyl, tert-butyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl and 3,5-dimethyl-4-methoxyphen-1-yl.

14. A compound of formula I according to claim 1, wherein R$_2$ and R$_3$ are identical substituents and are a radical of formula II, and R$_{10}$ and R$_{11}$ are identical substituents and are phenyl, cyclohexyl, tert-butyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl or 3,5-dimethyl-4-methoxyphen-1-yl.

15. A compound of formula I according to claim 1, wherein $R_2$ and $R_3$ are identical substituents and are a radical of formula II, $R_{10}$ is phenyl and $R_{11}$ is cyclohexyl, 2- or 4-methylphen-1-yl, 2- or 4-methoxyphen-1-yl, 4-(dimethylamino)phen-1-yl, 2- or 4-methoxyphen-1-yl, 3,5-dimethyl-4-(dimethylamino)phen-1-yl, 3,5-dimethyl-4-methoxyphen-1-yl or 4-tert-butylphen-1-yl.

16. A compound of formula I according to claim 1, wherein $R_1$ is methyl, $R_2$ and $R_3$ are identical and are a radical of formula II, $R_{10}$ and $R_{11}$ are identical substituents and are phenyl or cyclohexyl.

17. A compound of formula I according to claim 1, wherein $R_2$, $R_3$, $R_{10}$ and $R_{11}$ are identical and are a radical of formula II.

18. A compound of formula I according to claim 1, wherein $R_1$ is methyl, $R_2$, $R_3$, $R_{10}$ and $R_{11}$ are identical and are a radical of formula II, $R_{12}$ is 4-trifluoromethyl or 3,5-di(trifluoromethyl) and n is 0.

19. A compound of formula I according to claim 1, wherein $R_1$ is methyl, $R_2$ and $R_3$ are identical and are a radical of formula II, $R_{10}$ and $R_{11}$ are phenyl, $R_{12}$ is 4-trifluoromethyl or 3,5-di(trifluoromethyl) and n is 0.

20. A compound of formula I according to claim 1, which is selected from the group consisting of
- {(R)-1-[(S)-2-bis(4-trifluoromethylphenyl)phosphino)ferrocenyl]}ethyl bis(3,5-dimethylphenyl)phosphine,
- {(R)-1-[(S)-2-bis(4-trifluoromethylphenyl)phosphino)ferrocenyl]}ethyl dicyclohexylphosphine,
- {(R)-1-[(S)-2-bis(3,5-bis(trifluoromethyl)phenyl)phosphino)ferrocenyl]}ethyl bis(3,5-dimethylphenyl)phosphine,
- {(R)-1-[(S)-2-bis(3,5-bis(trifluoromethyl)phenyl)phosphino)ferrocenyl]}ethyl diphenylphosphine, and
- {(R)-1-[(S)-2-bis(4-trifluoromethylphenyl)phosphino)ferrocenyl]}ethyl diphenylphosphine.

21. A process for the preparation of a compound of formula I according to claim 1, which comprises either reacting a compound of formula III

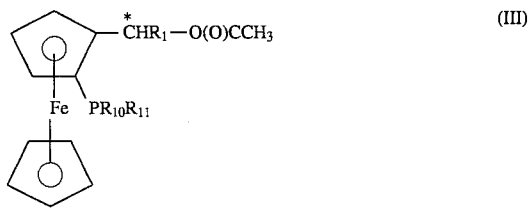

in the presence of an inert solvent, at room temperature or elevated temperature, with a phosphine of formula IV

or reacting a compound of formula VII

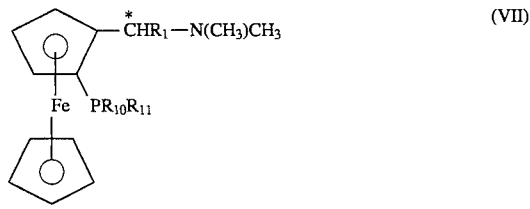

wherein $R_1$, $R_{10}$ and $R_{11}$ are as defined for formula I, in the presence of an inert solvent, at room temperature or elevated temperature, with a phosphine of formula IV

wherein $R_1$, $R_2$, $R_3$, $R_{10}$ and $R_{11}$ are as defined in claim 1.

* * * * *